United States Patent
King et al.

(10) Patent No.: US 11,554,154 B2
(45) Date of Patent: Jan. 17, 2023

(54) POLYGALA EXTRACT FOR THE TREATMENT OF MAJOR DEPRESSIVE DISORDER

(71) Applicant: BioLite, Inc., Taipei (TW)

(72) Inventors: Chi-Hsin Richard King, Taipei (TW); Hsien-Ming Wu, Taipei (TW); Howard Doong, Taipei (TW); Tsung-Shann Jiang, Taipei (TW)

(73) Assignee: BIOLITE, INC., Taipei (TW)

( * ) Notice: Subject to any disclaimer, the term of this patent is extended or adjusted under 35 U.S.C. 154(b) by 0 days.

(21) Appl. No.: 16/936,032

(22) Filed: Jul. 22, 2020

(65) Prior Publication Data

US 2022/0023373 A1   Jan. 27, 2022

(51) Int. Cl.
  *A61K 36/69*   (2006.01)
  *A61K 9/48*    (2006.01)
  *A61P 25/24*   (2006.01)
  *A61K 9/00*    (2006.01)

(52) U.S. Cl.
  CPC .............. *A61K 36/69* (2013.01); *A61K 9/485* (2013.01); *A61P 25/24* (2018.01); *A61K 9/0053* (2013.01); *A61K 2236/331* (2013.01); *A61K 2236/333* (2013.01)

(58) Field of Classification Search
  None
  See application file for complete search history.

(56) References Cited

U.S. PATENT DOCUMENTS

| | | | | |
|---|---|---|---|---|
| 5,589,182 A | * | 12/1996 | Tashiro | A61K 36/232 424/423 |
| 6,911,222 B2 | * | 6/2005 | Ko | A61K 36/69 424/773 |
| 7,507,424 B2 | * | 3/2009 | Mitra | A61K 36/48 424/725 |

OTHER PUBLICATIONS

Chen (Nutrients (Apr. 2019), vol. 11, 859, pp. 1-14) (Year: 2019).*
Fantino (BMC Psychiatry (2019), vol. 9, No. 26, 6 pages) (Year: 2009).*

* cited by examiner

*Primary Examiner* — Susan Hoffman
(74) *Attorney, Agent, or Firm* — Muncy, Geissler, Olds & Lowe, P.C.

(57) ABSTRACT

This invention relates to a method of treating Major depressive disorder by orally administering to a subject a composition containing a Radix Polygalae (*Polygala tenuifolia* Willd) extract (PDC-1421). A solid dosage form of PDC-1421 can be prepared into the gelatin capsule. The oral administration of PDC-1421 in healthy volunteers was safe and well-tolerated for the daily dose from 380 mg to 3800 mg. The composition can be administered chronically over at least 25 days; the daily dose is administered once per day, twice per day, or three times per day, wherein each dose is 380-760 mg of the botanical extraction.

11 Claims, 1 Drawing Sheet

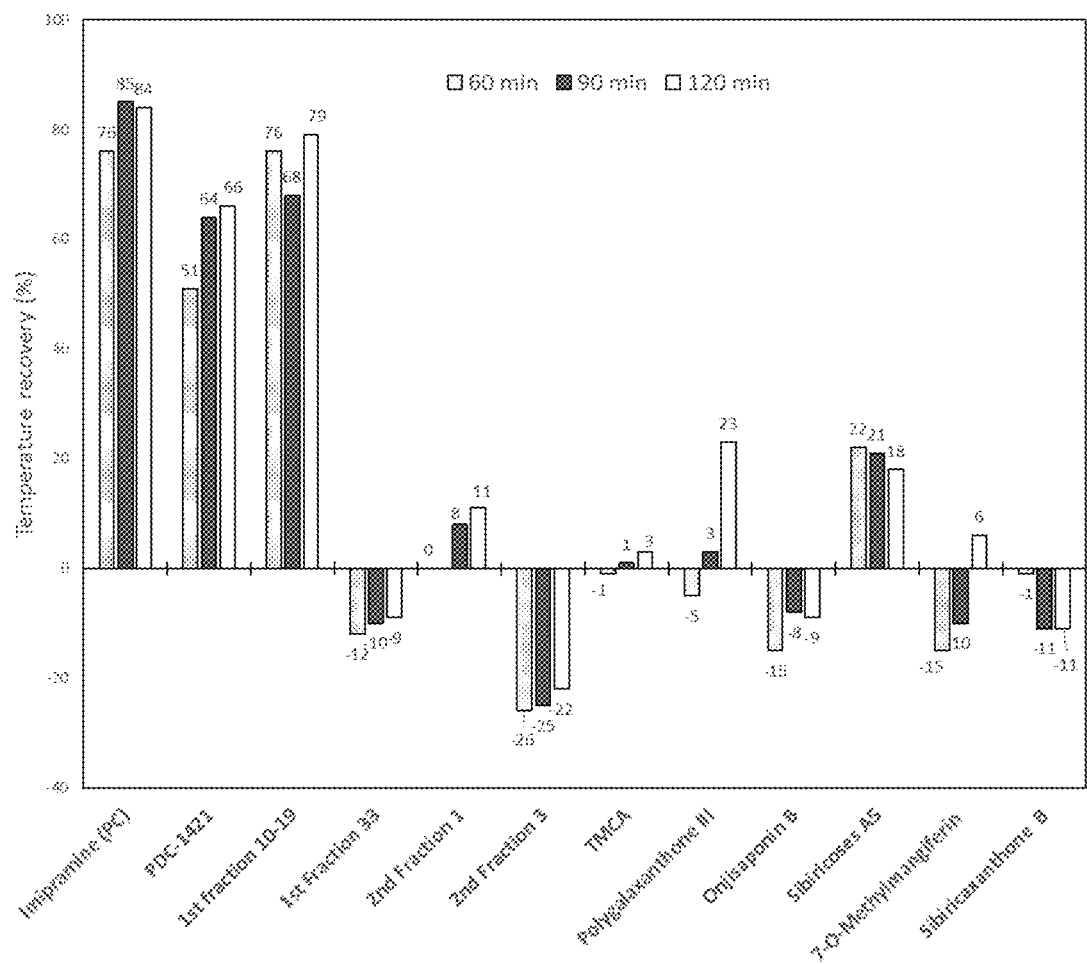

POLYGALA EXTRACT FOR THE TREATMENT OF MAJOR DEPRESSIVE DISORDER

BACKGROUND OF THE INVENTION

Technical Field of the Invention

This invention relates to a method of treating major depressive disorder by orally administering to a subject a composition containing a Radix Polygalae (*Polygala tenuifolia* Willd) extract.

Background

Major depressive disorder affected approximately 216 million people (3% of the world's population) in 2015 (GBD 2015 Disease and Injury Incidence and Prevalence Collaborators (October 2016). "Global, regional, and national incidence, prevalence, and years lived with disability for 310 diseases and injuries, 1990-2015: a systematic analysis for the Global Burden of Disease Study 2015". *Lancet*. 388 (10053): 1545-602; Classified in the DSM-IV-TR (Diagnostic and Statistical Manual of Mental Disorders, Fourth Edition, Text Revision, American Psychiatric Association, Washington D.C., 2000)).

Even though patients with depression have been treated with first-line antidepressants such as selective serotonin reuptake inhibitors (SSRIs), 40~50% of patients do not respond to the antidepressant administered3. Furthermore, recurrence of depressive episode makes mortality and attempted suicide rate elevated to 21% (Sartorius N, Angstt J. Suicide in population subgroups. *Int Clin Psychopharmacol*. 2001; 16 Suppl 2: 2p preceding S1.). Therefore, a new type of antidepressant with higher efficacy and safety are needed for the treatment of depression.

SUMMARY OF INVENTION

Accordingly, the present invention provides a method of treating major depressive disorder (MDD) comprising orally administering to a subject in need thereof a composition containing an amount of a botanical extraction at daily dose of 380-3800 mg; wherein the botanical extraction is one or a combination of: i) a polar solvent extract of *Polygala*, the polar solvent being water or a mixture of water and methanol or ethanol; ii) an aqueous fraction resulting from an extraction of the polar solvent extract with an organic solvent; iii) an organic eluent by introducing the polar solvent extract or the aqueous fraction into a reverse phase chromatography column, and eluting the column with water and an organic solvent; and iv) a filtrate having a molecular mass less than 30,000 in the organic eluent.

In some embodiments, the composition is administered in an oral dosage form.

In some embodiments, the composition further contains silicon dioxide and magnesium stearate and is in the form of a capsule.

In some embodiments, the composition is administered at the onset of an episode of a symptom of the depressive disorder.

In some embodiments, the composition is administered chronically.

In some embodiments, the composition is administered on a schedule throughout the day.

In some embodiments, the said daily dose is administered once per day, twice per day, or three times per day.

In some embodiments, each dose is 380-760 mg of the botanical extraction.

In some embodiments, the administration is daily over at least 25 days.

In some embodiments, the said subject is under evaluation at the end of administration and after at least one month thereafter.

The said evaluation comprises administering and evaluating the results of the Montgomery-Asberg Depression Rating Scale (MADRS) and/or the Hamilton Depression Rating Scale (HAM-D-17) and/or the Hamilton Anxiety Rating Scale (HAM-A) and/or the Clinical Global Impression Scale (CGI), and/or the Columbia-Suicide Severity Rating Scale (C-SSRS).

BRIEF DESCRIPTION OF THE DRAWINGS

FIG. 1 depicts in vivo tetrabenazine-induced hypothermia test. Imipramine (positive control), PDC-1421, 1st Fraction 10-19, 1st Fraction 33, 2nd Fraction-1 (the major components are polygalatenosides A/B/C), 2nd Fraction-3, TMCA, Polygalaxanthone III, Onjisaponin B, Sibiricose A5, 7-O-Methylmangiferin and Sibiricaxanthone B are administered as test substances and the temperature recovery (%) is documented as shown in figure.

DETAILED DESCRIPTION OF THE INVENTION

All of the features disclosed in this specification may be combined in any combination. An alternative feature serving the same, equivalent, or similar purpose may replace each feature disclosed in this specification. Thus, unless expressly stated otherwise, each feature disclosed is only an example of a generic series of equivalent or similar features.

List of Abbreviations/Definitions
AE Adverse Events
CGI Clinical Global Impression Scale
C-SSRS Columbia-Suicide Severity Rating Scale
DSSS Depression and Somatic Symptoms Scale
HAM-D-17 Hamilton Depression Rating Scale
HAM-A Hamilton Anxiety Rating Scale
MADRS Montgomery and Asberg Depression Rating Scale
NRI Norepinephrine Reuptake Inhibitor

EXAMPLE 1

Preparation of Radix Polygalae (*Polygala tenuifolia* Willd) Extract PDC-1421

Dry whole root of *P. tenuifolia* Willd is cooked in water for twice with a ratio of 100 kg to 800 kg under refluxing for one hour and a ratio of 100 kg to 700 kg under refluxing for another one hour. An aqueous extract is obtained after mixing the two cooked mixture. The aqueous extract is concentrated to 400 kg by evaporation in vacuo, and filtered by centrifugal filter. Then, the resulting concentrate is filtered by the resin column for chromatography. The specific filtering eluent is collected. The eluent concentrated to by evaporation in vacuo and dried by spray drier to yield a powder product PDC-1421.

EXAMPLE 2

In Vivo Tetrabenazine-Induced Hypothermia Assay

The around 70% of PDC-1421 in Example 1 are composed of sucroester (34%), saponin (18%) and xanthone (17%). Some active compounds of powder product in Example 1, polygalatenosides A/B/C (2nd fraction 1), ploygalaxanthone III, sibiricoses A5, and 7-O-methylmangiferin are also discovered through in vivo tetrabenazine-induced hypothermia test (one of rodent models for evaluating antidepressant-like activity in mice). Imipramine (positive control), PDC-1421, 1st Fraction 10-19, 1st Fraction 33, 2nd Fraction-1 (the major components are polygalatenosides A/B/C), 2nd Fraction-3, TMCA, Polygalaxanthone III, Onjisaponin B, Sibiricose A5, 7-O-Methylmangiferin and Sibiricaxanthone B were dissolved in water for injection (WFI) and administered by oral gavage. The dosing volume was 10 mL/kg. Test substances and vehicle (WFI) were administered by oral gavage to groups of 8 ICR male mice weighing 23±3 g 60 minutes before intraperitoneal injection of tetrabenazine (TBZ, 85 ma/kg). Body temperature was recorded before (0 min), and 60, 90 and 120 min after TBZ challenge. The temperature recovery (%) of test substances is shown in the FIG. 1.

EXAMPLE 3

Preclinical Study for Recommended Dosage and Route of Administration

Determination of initial dose is critical when a new drug is administered to human first time. Based on the FDA's guidance documents, NOAELs from toxicity studies were used to estimate the starting dose in our study. Table 2 summarizes the MRSD for 60 kg human/day calculated from the NOAEL of 28 day repeating dose studies in rats and in dogs using safety margin at 75-fold.

TABLE 1

Calculation of starting dose

| Study | Species | Dosage | HED | Dose for 60 kg human/day |
|---|---|---|---|---|
| 28-day repeated dose subacute oral toxicity study in rats | Rat | 3000 mg/kg (NOAEL) | 483.9 mg/kg | 387 mg/day (MRSD) |
| 28-day repeated dose subacute oral toxicity study in dogs | Dog | 3000 mg/kg (NOAEL) | 1666.7 mg/kg | 1333 mg/day (MRSD) |

NOAEL: No observable adverse effect level
HED: Human equivalent dose
MRSD: Maximum recommended starting dose
*The calculation of HED and MRSD are referred to FDA document.

Based on these calculations, we proposed the starting dose of PDC-1421 to be at 380 mg/day. In the proposed Phase I study, a single dose of PDC-1421 (oral administration) will be used to evaluate the safety when taken by healthy subjects. The starting dose and dosage regimen are 380 mg PDC-1421 (one capsule of PDC-1421 Capsule) once daily after meal.

EXAMPLE 4

Preparation of PDC-1421 Capsule

A solid dosage form of Radix Polygalae (*Polygala tenuifolia* Willd) extract (PDC-1421) can be prepared into the gelatin capsule by conventional techniques known to those skilled in the art. In a preferred embodiment of the invention, the matrix comprises two excipients, the first of which, silicon dioxide served as a glidant may constitutes from about 2 to 10%, more preferably 5% of filling. The second excipient, Magnesium stearate served as a lubricant may constitutes from about 2 to 10%, more preferably 5% of filling.

TABLE 2

Composition of PDC-1421 Capsule

| Name of Ingredient | mg per Capsule | Function |
|---|---|---|
| PDC-1421 | 380 mg | Active ingredient |
| Silicon dioxide | 10 mg | Excipient |
| Magnesium stearate | 10 mg | Excipient |

EXAMPLE 5

Phase I in Healthy Subject

In phase I trial, all total of 85 subjects were screened at study site and 30 subjects were enrolled. They were 9 subjects in cohort A with 7 administered PDC-1421 (380 mg) and 2 administered placebo, 1 of 7 PDC-1421 subjects had no laboratory test data at baseline; 8 subjects in cohort B with 6 administered PDC-1421 (1140 mg) and 2 administered placebo; 4 subjects in cohort C with 3 administered PDC-1421 (2280 mg) and 1 administered placebo; 9 subjects in cohort D with 7 administered PDC-1421(3800 mg) and 2 administered placebo, 1 of 7 PDC-1421 subjects had abnormal laboratory data at screening visit.

Physical examination was determined to be "normal" on every Body System in each cohort and no subject had DLT and toxicity grade.

All of the changes of vital signs from baseline of PDC-1421 and placebo group were mild and did not exceed the limit of normal range. Furthermore, all of the toxicity grades of vital signs were the lowest, systolic blood pressure in grade 1, increase>20 mm/Hg than baseline at 4 hours. No medical intervention/therapy was required. There is no correlation of changes from baseline or changes in the toxicity grade of vital signs between doses of PDC-1421.

All changes of laboratory test data from baseline of PDC-1421 group were mild and no clinically significant deviation from the normal range. Furthermore, the toxicity grades of laboratory test data of PDC-1421 and placebo groups were the lowest, grade 1. No medical intervention/therapy was required. There was no correlation of change from baseline or change in the toxicity grade of laboratory test between doses of PDC-1421. Only two grade 2 toxicity (at 24 hours in glucose in cohort A and at 4 hours in glucose in cohort B) occurred in placebo group and no medical intervention/therapy were required for these cases.

ECG was determined to be "normal" in each time point and in each cohort. No subject had DLT and toxicity grade. C-SSRS were all 0 point on Suicidal ideation, Intensity of ideation, Suicidal behavior in each cohort.

No subject had serious adverse event and no subject discontinued due to adverse event, no clinically significant finding in physical examinations, vital signs, electrocardiogram, laboratory measurements, and C-SSRS was observed throughout the treatment period, and the oral administration of PDC-1421 in healthy volunteers was safe and well-tolerated for the dose from 380 mg to 3800 mg. During the treatment period, 5 subjects reported to experience 8 mild adverse events shown as Table 3. The severity of these 5 adverse events was all mild and no medical action required. There was no correlation of number, severity, relationship and outcome of adverse events found between doses of PDC-1421 and placebo. Further, there was no deviation of electrolyte level and no significant gastrointestinal discomfort during monitoring in the clinical trial. There were two mild adverse events such as lower heart rate and higher systolic blood pressure. Lower heart rate was that coupled to the dog telemetry study but not higher systolic blood pressure.

TABLE 3

Frequencies of Adverse Events

| Adverse events BODY System | Frequency | | | | |
|---|---|---|---|---|---|
| | Cohort A (380 mg) N = 7 | Cohort B (1140 mg) N = 6 | Cohort C (2280 mg) N = 3 | Cohort D (3800 mg) N = 7 | Placebo N = 7 |
| Digest System | 3/7 | 0 | 0 | 0 | 1/7 |
| FLATULENCE | 2/7 | 0 | 0 | 0 | 1/7 |
| CONSTIPATION | 1/7 | 0 | 0 | 0 | 0 |
| Nervous System | 0 | 0 | 2/3 | 0 | 2/7 |
| SOMNOLENCE | 0 | 0 | 1/3 | 0 | 2/7 |
| STOMATITIS ULCER | 0 | 0 | 1/3 | 0 | 0 |

In summary, no subject had serious adverse event and no subject discontinued due to adverse event. No clinically significant findings in physical examinations, vital signs, electrocardiogram, laboratory measurements, and C-SSRS was observed throughout the treatment period. The oral administration of PDC-1421 in healthy volunteers was safe and well-tolerated for the dose from 380 mg to 3800 mg.

EXAMPLE 6

Phase II in Major Depressive Disorder (MDD) Patients

This Phase II clinical trial was aimed to evaluate the safety and efficacy of PDC-1421 in adults with MDD. This study included two parts. The Part I study was a multiple center, open label, dose escalation evaluation with two dosage levels (1 or 2 capsules TID; 1140 mg or 2280 mg per day) sequentially. The Part II study was a multiple center, randomized (1:1:1), double-blind, placebo-controlled, parallel groups with three study arms to compare efficacy and safety profiles of PDC-1421 Capsule at two dosage levels (either 1 or 2 capsules TID) versus control (placebo TID).

The primary objective was to assess the efficacy profile of PDC-1421 Capsule in major depressive disorder (MDD) with Montgomery-Asberg Depression Rating Scale (MADRS). The secondary objective was to evaluate the efficacy and safety profile of PDC-1421 Capsule in MDD with other rating scales.

In Part I, 12 subjects were randomized to Cohort 1 (low-dose group, N=6) and Cohort 2 (high-dose group, N=6). All subjects completed the study, and no subject withdrew from Part I. In Part II, 60 subjects (50 at Taiwan sites and 10 at United State site) were randomized to 3 study arms: (1) Low-dose group (N=19), (2) High-dose group (N=19) and (3) Placebo group (N=20). A total of 48 subjects completed and 12 subjects withdrew from the study (Low-dose group: N=5: High-dose group: N=2; Placebo group: N=5).

Efficacy Results

In the ITT population, net changes in MADRS from baseline to Week 6 were −9.21, −13.19, and −9.20 for Low-dose group, High-dose group and Placebo group, respectively. In the PP population, net changes in MADRS from baseline to Week 6 were −10.40, −13.40, and −8.64 for three treatment arms respectively. The greater reduction in mean score of MADRS was observed in the High-dose group compared to Low-dose group and Placebo group in both ITT and PP populations, but the group difference did not reach statistical significance.

The net changes in MADRS, HAM-D-17, HAM-A, DSSS-depression, and CGI-severity and response rates in MADRS and HAM-D-17 at Week 6 in ITT population were summarized in the below table 4.

TABLE 4

The efficacy results at Week 6 in ITT population

| Net change | Treatment Group | Sample Size | Net change at Week 6 | | | | |
|---|---|---|---|---|---|---|---|
| | | | Mean | SD | Median | (Min, Max) | P-value[1] |
| MADRS | Low-dose | 19 | −9.21 | 8.32 | −9.00 | (−27, 11) | 0.393 |
| | High-dose | 21 | −13.19 | 9.68 | −12.00 | (−30, −1) | |
| | Placebo | 20 | −9.20 | 7.98 | −9.00 | (−21, 5) | |
| HAM-D-17 | Low-dose | 19 | −8.84 | 7.21 | −11.00 | (−21, 7) | 0.406 |
| | High-dose | 21 | −10.95 | 6.71 | −13.00 | (−21, 3) | |
| | Placebo | 20 | −8.70 | 6.91 | −9.00 | (−21, 7) | |
| HAM-A | Low-dose | 19 | −7.00 | 7.46 | −8.00 | (−18, 8) | 0.459 |
| | High-dose | 21 | −8.71 | 6.04 | −8.00 | (−19, 2) | |
| | Placebo | 20 | −6.20 | 6.30 | −5.00 | (−18, 3) | |
| DSSS-Depression | Low-dose | 19 | −5.89 | 5.18 | −5.00 | (−16, 2) | 0.496 |
| | High-dose | 21 | −4.71 | 7.71 | −4.00 | (−22, 8) | |
| | Placebo | 20 | −3.55 | 5.09 | −3.50 | (−13, 7) | |

TABLE 4-continued

The efficacy results at Week 6 in ITT population

| CGI-Severity | Low-dose | 19 | −1.00 | 1.00 | −1.00 | (−3, 1) | 0.471 |
| --- | --- | --- | --- | --- | --- | --- | --- |
| | High-dose | 21 | −1.33 | 1.20 | −1.00 | (−3, 1) | |
| | Placebo | 20 | −0.90 | 1.02 | −1.00 | (−2, 1) | |

| | | | Week 6 | | |
| --- | --- | --- | --- | --- | --- |
| Responder from Baseline | Treatment Group | Sample Size | Number of responder | % | P-value[2] |
| MADRS | Low-dose | 19 | 6 | 32% | 0.230 |
| | High-dose | 21 | 11 | 52% | |
| | Placebo | 20 | 7 | 35% | |
| HAM-D-17 | Low-dose | 19 | 9 | 47% | 0.930 |
| | High-dose | 21 | 12 | 57% | |
| | Placebo | 20 | 8 | 40% | |

[1]Kruskal-Wallis test
[2]Cochran-Mantel-Haenszel test

In the ITT population the net changes in HAM-D-17 from baseline to Week 6 were −8.8, −11.0, and −8.7 for Low-dose group, High-dose group and Placebo group, respectively. In the PP population, net changes in HAM-D-17 from baseline to Week 6 were −10.0, −11.1, and −7.9 for three treatment arms, respectively. The greater reduction in mean score of HAM-D-17 was observed in the High-dose group compared to Low-dose group and Placebo group in both ITT and PP populations, but the group difference did not reach statistical significance (P=0.406 for ITT; P=0.392 for PP).

A significant group difference on net change in HAM-D-17 and HAM-A in ITT population at Week 2 was found between three groups (P=0.038 for HAM-D-17; P=0.041 for HAM-A). Post-hoc pair-wise comparisons demonstrated a significant difference between High-dose group and Placebo group in HAM-D-17 (High-dose vs. Placebo=−7.90 vs. −4.30; Adjusted P=0.039) and HAM-A (−5.38 vs. −2.90, Adjusted P=0.022), but not for Low-dose group versus Placebo, suggesting that subjects who took 2 PDC-1421 Capsules TID showed greater improvement compared with those in the Placebo group by Week 2 (net change=3.6 for HAM-D-17; 2.48 for HAM-A).

At Week 6, for MADRS, no significant group difference was observed in response rate in ITT population (P=0.230) and a nearly significant difference in PP population (P=0.062). Percentage of "responders" at Week 6 was highest in High-dose group (Low-dose vs. High-dose vs. Placebo=32% [n=6] vs. 52% [n=11] vs. 35% [n=7] in ITT population; 33% [n=5] vs. 53% [n=8] vs. 29% [n=4] in PP population).

At Week 2, for HAM-D-17, a significant group difference was found between three treatment groups in both ITT and PP population (P=0.028 and 0.037, respectively). Percentages of "responders" were highest in the Low-dose group, followed by High-dose and Placebo groups in ITT and PP populations (Low-dose vs. High-dose vs. Placebo=26% vs. 14% vs. 10% in ITT; 27% vs. 20% vs. 14% in PP).

Safety Results

The safety evaluation was based on the ITT population, who took at least one dose of the IPs and had any of the post-baseline safety data collected.

Regarding the incidence of TEAEs, a total 4 subjects (33.3%) experienced at least one TEAE with 2 subjects in each dose cohort in Part I study; a total of 32 subjects (53.3%) experienced at least one TEAE with 12 (63.2%) in the Low-dose group, 11 (52.4%) in the High-dose group, and 9 (45.0%) in the Placebo group for Part II study.

For more common TEAEs, the most frequently reported TEAEs in Part I included "Infections and infestations" (Total: n=2 [16.7%]; Low-dose: n=1; High-dose: n=1) and "Psychiatric disorders" (Total: n=2 [16.7%]; Low-dose: n=0; High-dose: n=2). In Part II, the most commonly reported TEAEs included "Gastrointestinal disorders" (Total: n=17 [28.3%], Low-dose: n=7; High-dose: n=5; Placebo: n=5), "Nervous system disorders" (Total: n=4 [6.7%]; Low-dose: n=1; High-dose: n=2; Placebo: n=1) and "Psychiatric disorders" (Total: n=4 [6.7%]; Low-dose: n=3; High-dose: n=0; Placebo: n=1). Among TEAEs with incidence ≥5%, more subjects reported "Dry mouth" in both Low-dose and High-dose treatment groups (n=3 for each group) than those in the Placebo group (n=1).

For level of severity, a total of 6 TEAEs were rated as mild or moderate in Part I study; a total of 68 TEAEs were recorded in Part II study (No. of events: Low-dose group vs. High-dose group vs. Placebo group=20 vs. 26 vs. 22), with 53 events rated as mild (19 vs. 17 vs. 17), 14 events as moderate (1 vs. 9 vs. 4) and 1 event rated as severe in Placebo group. No deaths or SAEs occurred in this study.

For occurrence of AE in the withdrawals, two withdrawn subjects (Low-dose group: n=1; Placebo group: n=1) were due to depression, and one subject (Low-dose group) was due to anxiety and this event was judged to be unlikely related to the test product by the PI. These AEs might be condition related, but not treatment related.

Regarding the laboratory values at each scheduled visit, few abnormal values with clinical significance (CS) were observed in either Part I or Part II study. The highest incidence of abnormalities with CS was on triglyceride (Part I: n=1 in High-dose group; Part II: n=3 in High-dose group).

For vital signs and ECG, no subject was evaluated as abnormalities with CS in Part I study. For Part II study, abnormal SBP and DBP with CS were detected in the High-dose group (SBP at Week 4 and Week 6: n=1; DBP from baseline to Week 7: n=1). All of these abnormal blood pressure events were detected in the same subject with a hypertension medical history. All other values were evaluated as normal or abnormal with non-clinical significance (NCS), without changing to abnormality with CS for either vital signs or ECG.

For physical examination, no subject was changed from normal to abnormal (NCS or CS) for all the scheduled visits in both Part I and Part II studies, suggesting that, no physical evaluation became worse during treatment and follow-up period.

With regard to the assessment of suicidal ideation and behavior, incidence of 'suicidal ideation' and 'suicidal ideation or suicidal behavior' based on C-SSRS were low and similar between two groups in the Part I study with around 1 to 2 subjects; no 'suicidal behavior' was observed during treatment. For Part II, 'suicidal behavior' was not observed in any of the three groups. These results suggest that treatment of PDC-1421 did not increase the risk of either suicidal ideation or suicidal behavior.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

TABLE 5

The score changes of all rating scales from baseline to Week 2, 4, 6 and 7 - ITT population, Part II

| Scale | | Treatment Group | N | Week 2 Mean (SD) | Median (IQR) | (Min, Max) | P-value[1] | Post-hoc P-value[2] | P-value[3] |
|---|---|---|---|---|---|---|---|---|---|
| MADRS | | Low-dose | 19 | −6.4 (8.87) | −5.0 (9.0) | (−27.0, 9.0) | 0.487 | NA | NA |
| | | High-dose | 21 | −7.4 (5.08) | −7.0 (8.0) | (−17.0, 1.0) | | | |
| | | Placebo | 20 | −5.5 (5.76) | −4.0 (9.0) | (−19.0, 2.0) | | | |
| HAM-D-17 | | Low-dose | 19 | −6.5 (6.22) | −5.0 (7.0) | (−21.0, 5.0) | 0.038* | 0.090[a] | 0.090[a] |
| | | High-dose | 21 | −7.9 (4.72) | −9.0 (7.0) | (−16.0, 1.0) | | 0.020[b]* | 0.039[b]* |
| | | Placebo | 20 | −4.3 (4.58) | −3.0 (4.0) | (−17.0, 3.0) | | | |
| HAM-A | | Low-dose | 19 | −4.3 (5.45) | −2.0 (7.0) | (−18.0, 6.0) | 0.041* | 0.409[a] | 0.409[a] |
| | | High-dose | 21 | −5.4 (3.06) | −6.0 (4.0) | (−10.0, 2.0) | | 0.011[b]* | 0.022[b]* |
| | | Placebo | 20 | −2.9 (4.66) | −2.0 (4.0) | (−16.0, 5.0) | | | |
| DSSS | Depression | Low-dose | 19 | −3.1 (6.35) | −2.0 (9.0) | (−14.0, 12.0) | 0.425 | NA | NA |
| | | High-dose | 21 | −3.6 (5.26) | −3.0 (5.0) | (−14.0, 9.0) | | | |
| | | Placebo | 20 | −1.7 (3.15) | −1.0 (4.0) | (−7.0, 5.0) | | | |
| | Somatic | Low-dose | 19 | −2.2 (4.11) | −2.0 (5.0) | (−9.0, 10.0) | 0.512 | | |
| | | High-dose | 21 | −2.3 (4.56) | −1.0 (4.0) | (−17.0, 4.0) | | | |
| | | Placebo | 20 | −1.1 (2.74) | −1.0 (2.5) | (−7.0, 5.0) | | | |
| | Pain | Low-dose | 19 | −1.0 (2.36) | −1.0 (2.0) | (−5.0, 6.0) | 0.473 | | |
| | | High-dose | 21 | −0.9 (2.46) | 0.0 (2.0) | (−7.0, 3.0) | | | |
| | | Placebo | 20 | −0.4 (2.01) | 0.0 (1.0) | (−5.0, 4.0) | | | |
| CGI | CGI-S | Low-dose | 19 | −0.7 (0.95) | 0.0 (1.0) | (−3.0, 0.0) | 0.126 | | |
| | | High-dose | 21 | −0.6 (0.50) | −1.0 (1.0) | (−1.0, 0.0) | | | |
| | | Placebo | 20 | −0.3 (0.57) | 0.0 (0.5) | (−2.0, 0.0) | | | |
| | CGI-I (original score) | Low-dose | 19 | 3.1 (1.03) | 3.0 (2.0) | (1.0, 5.0) | 0.206 | | |
| | | High-dose | 21 | 3.0 (0.84) | 3.0 (1.0) | (2.0, 5.0) | | | |
| | | Placebo | 20 | 3.4 (0.60) | 3.0 (1.0) | (2.0, 4.0) | | | |

| Scale | | Treatment Group | Week 4 Mean (SD) | Median (IQR) | (Min, Max) | P-value[1] |
|---|---|---|---|---|---|---|
| MADRS | | Low-dose | −7.6 (9.12) | −9.0 (8.0) | (−27.0, 11.0) | 0.536 |
| | | High-dose | −10.8 (7.95) | −9.0 (12.0) | (−24.0, 1.0) | |
| | | Placebo | −8.7 (7.07) | −9.5 (9.5) | (−21.0, 8.0) | |
| HAM-D-17 | | Low-dose | −7.5 (6.64) | −8.0 (9.0) | (−21.0, 7.0) | 0.475 |
| | | High-dose | −9.7 (6.03) | −11.0 (10.0) | (−18.0, 1.0) | |
| | | Placebo | −8.2 (4.72) | −8.0 (7.0) | (−18.0, 0.0) | |
| HAM-A | | Low-dose | −5.5 (6.55) | −6.0 (8.0) | (−18.0, 8.0) | 0.782 |
| | | High-dose | −7.2 (5.95) | −8.0 (11.0) | (−16.0, 1.0) | |
| | | Placebo | −6.2 (4.82) | −5.0 (7.0) | (−16.0, 0.0) | |
| DSSS | Depression | Low-dose | −5.6 (5.58) | −4.0 (9.00) | (−16.0, 3.0) | 0.730 |
| | | High-dose | −4.5 (5.36) | −4.0 (5.00) | (−18.0, 3.0) | |
| | | Placebo | −4.0 (5.20) | −3.0 (5.50) | (−14.0, 5.0) | |
| | Somatic | Low-dose | −3.3 (3.38) | −4.0 (5.0) | (−9.0, 5.0) | 0.060 |
| | | High-dose | −2.6 (5.30) | −1.0 (5.0) | (−15.0, 6.0) | |
| | | Placebo | −0.9 (2.21) | −1.0 (2.0) | (−6.0, 5.0) | |
| | Pain | Low-dose | −1.4 (2.01) | −2.0 (3.0) | (−4.0, 4.0) | 0.393 |
| | | High-dose | −1.2 (2.79) | −1.0 (2.0) | (−9.0, 3.0) | |
| | | Placebo | −0.6 (1.93) | −0.5 (1.50) | (−5.0, 4.0) | |
| CGI | CGI-S | Low-dose | −0.9 (1.20) | −1.0 (1.0) | (−3.0, 1.0) | 0.596 |
| | | High-dose | −1.1 (0.77) | −1.00 (1.0) | (−2.0, 0.0) | |
| | | Placebo | −0.9 (0.72) | −1.0 (1.0) | (−2.0, 0.0) | |
| | CGI-I (original score) | Low-dose | 3.1 (1.49) | 3.0 (2.0) | (1.0, 6.0) | 0.665 |
| | | High-dose | 2.8 (0.94) | 2.0 (1.0) | (2.0, 5.0) | |
| | | Placebo | 2.9 (0.85) | 3.0 (1.0) | (2.0, 5.0) | |

TABLE 5-continued

The score changes of all rating scales from baseline to Week 2, 4, 6 and 7 - ITT population, Part II

| Scale | | Treatment Group | N | Week 6 Mean (SD) | Median (IQR) | (Min, Max) | P-value[1] |
|---|---|---|---|---|---|---|---|
| MADRS | | Low-dose | 15 | −9.2 (8.32) | −9.0 (13.0) | (−27.0, 11.0) | 0.393 |
| | | High-dose | 15 | −13.2 (9.68) | −12.0 (13.0) | (−30.0, −1.0) | |
| | | Placebo | 14 | −9.2 (7.98) | −9.0 (13.5) | (−21.0, 5.0) | |
| HAM-D-17 | | Low-dose | 15 | −8.8 (7.21) | −11.0 (10.0) | (−21.0, 7.0) | 0.406 |
| | | High-dose | 15 | −11.00 (6.71) | −13.0 (12.0) | (−21.0, 3.0) | |
| | | Placebo | 14 | −8.7 (6.91) | −9.0 (10.0) | (−21.0, 7.0) | |
| HAM-A | | Low-dose | 15 | −7.0 (7.46) | −8.0 (12.0) | (−18.0, 8.0) | 0.459 |
| | | High-dose | 15 | −8.7 (6.04) | −8.0 (10.0) | (−19.0, 2.0) | |
| | | Placebo | 14 | −6.2 (6.30) | −5.0 (10.0) | (−18.0, 3.0) | |
| DSSS | Depression | Low-dose | 15 | −5.9 (5.18) | −5.0 (7.0) | (−16.0, 2.0) | 0.496 |
| | | High-dose | 15 | −4.7 (7.71) | −4.0 (8.0) | (−22.0, 8.0) | |
| | | Placebo | 14 | −3.6 (5.09) | −3.5 (4.50) | (−13.0, 7.0) | |
| | Somatic | Low-dose | 15 | −3.3 (3.94) | −3.0 (7.0) | (−10.0, 6.0) | 0.500 |
| | | High-dose | 15 | −2.9 (6.24) | −1.0 (7.0) | (−18.0, 5.0) | |
| | | Placebo | 14 | −2.3 (2.31) | −2.0 (2.0) | (−7.0, 1.0) | |
| | Pain | Low-dose | 15 | −1.4 (1.89) | −2.0 (3.0) | (−4.0, 4.0) | 0.724 |
| | | High-dose | 15 | −1.3 (3.23) | −1.0 (3.0) | (−9.0, 4.0) | |
| | | Placebo | 14 | −1.2 (1.76) | −0.5 (2.5) | (−5.0, 1.0) | |
| CGI | CGI-S | Low-dose | 15 | −1.0 (1.00) | −1.0 (2.0) | (−3.0, 1.0) | 0.471 |
| | | High-dose | 15 | −1.3 (1.20) | −1.0 (2.0) | (−3.0, 1.0) | |
| | | Placebo | 14 | −0.9 (1.02) | −1.0 (2.0) | (−2.0, 1.0) | |
| | CGI-I (original score) | Low-dose | 15 | 2.8 (1.18) | 3.0 (1.0) | (1.0, 6.0) | 0.936 |
| | | High-dose | 15 | 2.8 (1.44) | 3.0 (2.0) | (1.0, 6.0) | |
| | | Placebo | 14 | 2.9 (1.17) | 3.0 (1.0) | (1.0, 6.0) | |

| Scale | | Treatment Group | | Week 7 Mean (SD) | Median (IQR) | (Min, Max) | P-value[1] |
|---|---|---|---|---|---|---|---|
| MADRS | | Low-dose | | −8.2 (7.99) | −7.0 (12.0) | (−27.0, 11.0) | 0.175 |
| | | High-dose | | −13.6 (8.98) | −14.0 (13.0) | (−32.0, −1.0) | |
| | | Placebo | | −9.9 (7.32) | −10.0 (8.50) | (−23.0, 5.0) | |
| HAM-D-17 | | Low-dose | | −7.9 (7.05) | −8.0 (12.0) | (−21.0, 7.0) | 0.375 |
| | | High-dose | | −10.4 (6.23) | −11.0 (6.0) | (−22.0, 5.0) | |
| | | Placebo | | −8.7 (5.95) | −8.0 (9.50) | (−22.0, 0.0) | |
| HAM-A | | Low-dose | | −5.1 (7.15) | −4.0 (12.0) | (−18.0, 8.0) | 0.174 |
| | | High-dose | | −8.9 (5.82) | −8.0 (5.0) | (−22.0, 0.0) | |
| | | Placebo | | −6.6 (6.15) | −5.0 (11.50) | (−15.0, 3.0) | |
| DSSS | Depression | Low-dose | | −5.4 (5.46) | −5.0 (7.0) | (−16.0, 6.0) | 0.499 |
| | | High-dose | | −5.4 (6.46) | −6.0 (8.0) | (−18.0, 8.0) | |
| | | Placebo | | −3.3 (5.51) | −3.5 (7.0) | (−13.0, 7.0) | |
| | Somatic | Low-dose | | −3.2 (2.94) | −3.0 (6.0) | (−9.0, 1.0) | 0.223 |
| | | High-dose | | −3.1 (4.90) | −2.0 (5.0) | (−16.0, 3.0) | |
| | | Placebo | | −1.3 (2.62) | −1.0 (1.5) | (−8.0, 5.0) | |
| | Pain | Low-dose | | −1.3 (1.60) | −1.0 (2.0) | (−5.0, 1.0) | 0.207 |
| | | High-dose | | −1.3 (2.41) | −1.0 (3.0) | (−6.0, 3.0) | |
| | | Placebo | | −0.5 (1.88) | 0.0 (2.0) | (−4.0, 2.0) | |
| CGI | CGI-S | Low-dose | | −1.1 (0.99) | −1.0 (2.0) | (−3.0, 1.0) | 0.550 |
| | | High-dose | | −1.4 (1.12) | −1.0 (1.0) | (−4.0, 0.0) | |
| | | Placebo | | −1.0 (0.89) | −1.0 (2.0) | (−2.0, 1.0) | |
| | CGI-I (original score) | Low-dose | | 2.9 (1.15) | 3.0 (1.0) | (1.0, 6.0) | 0.433 |
| | | High-dose | | 2.6 (1.03) | 3.0 (1.0) | (1.0, 5.0) | |
| | | Placebo | | 3.0 (1.03) | 3.0 (1.5) | (2.0, 6.0) | |

[1]Kruskal-Wallis test;
[2]Wilcoxon rank sum test;
[3]Adjusted by Holm's procedure.
[a]Low-dose group vs. Placebo group;
[b]High-dose group vs. Placebo group.
*P < 0.05.
MADRS = Montgomery-Åsberg Depression Rating Scale; HAM-D-17 = Hamilton Rating Scale for Depression; HAM-A = Hamilton Rating Scale for anxiety; DSSS = Depression and Somatic Symptoms Scale; CGI = Clinical Global Impression; CGI-S = CGI-severity; CGI-I = CGI-improvement.

TABLE 6

The score change of all rating scales from baseline to Week 2, 4, 6 and 7 - PP population, Part II

| Scale | | Treatment Group | Sample size (N) | Week 2 | | | |
|---|---|---|---|---|---|---|---|
| | | | | Mean (SD) | Median (IQR) | (Min, Max) | P-value[1] |
| MADRS | | Low-dose | 15 | −6.5 (7.14) | −5.0 (8.0) | (−21.0, 5.0) | 0.629 |
| | | High-dose | 15 | −7.7 (4.99) | −7.0 (6.0) | (−17.0, 1.0) | |
| | | Placebo | 14 | −6.7 (5.93) | −4.5 (8.0) | (−19.0, 2.0) | |
| HAM-0-17 | | Low-dose | 15 | −6.6 (5.19) | −7.0 (7.0) | (−14.0, 5.0) | 0.105 |
| | | High-dose | 15 | −8.5 (5.10) | −10.0 (9.0) | (−16.0, 1.0) | |
| | | Placebo | 14 | −4.8 (5.18) | −3.0 (6.0) | (−17.0, 3.0) | |
| HAM-A | | Low-dose | 15 | −4.0 (4.74) | −2.0 (7.0) | (−12.00, 6.0) | 0.167 |
| | | High-dose | 15 | −5.4 (3.46) | −6.0 (4.0) | (−10.0, 2.0) | |
| | | Placebo | 14 | −2.9 (5.47) | −2.0 (5.0) | (−16.0, 5.0) | |
| DSSS | Depression | Low-dose | 15 | −3.4 (5.17) | −2.0 (9.0) | (−12.0, 7.0) | 0.920 |
| | | High-dose | 15 | −3.3 (5.75) | −4.0 (6.0) | (−14.0, 9.0) | |
| | | Placebo | 14 | −2.4 (3.08) | −3.0 (3.0) | (−7.0, 4.0) | |
| | Somatic | Low-dose | 15 | −2.9 (2.92) | −2.0 (5.0) | (−9.0, 1.0) | 0.343 |
| | | High-dose | 15 | −1.5 (3.50) | −1.0 (4.0) | (−10.0, 4.0) | |
| | | Placebo | 14 | −1.2 (3.24) | −1.0 (3.0) | (−7.0, 5.0) | |
| | Pain | Low-dose | 15 | −1.5 (1.81) | −1.0 (3.0) | (−5.0, 1.0) | 0.238 |
| | | High-dose | 15 | −0.4 (2.50) | 0.0 (2.0) | (−7.0, 3.0) | |
| | | Placebo | 14 | −0.6 (2.37) | −1.0 (2.0) | (−5.0, 4.0) | |
| CGI | CGI-S | Low-dose | 15 | −0.7 (0.82) | 0.0 (1.0) | (−2.0, 0.0) | 0.296 |
| | | High-dose | 15 | −0.7 (0.46) | −1.0 (1.0) | (−1.0, 0.0) | |
| | | Placebo | 14 | −0.4 (0.65) | 0.0 (1.0) | (−2.0, 0.0) | |
| | CGI-I (original score) | Low-dose | 15 | 3.0 (0.85) | 3.0 (2.0) | (2.0, 4.0) | 0.088 |
| | | High-dose | 15 | 2.7 (0.70) | 3.0 (1.0) | (2.0, 4.0) | |
| | | Placebo | 14 | 3.4 (0.63) | 3.0 (1.0) | (3.0, 4.0) | |

| Scale | | Treatment Group | | Week 4 | | | |
|---|---|---|---|---|---|---|---|
| | | | | Mean (SD) | Median (IQR) | (Min, Max) | P-value[1] |
| MADRS | | Low-dose | | −8.4 (7.00) | −9.0 (6.0) | (−24.0, 3.0) | 0.683 |
| | | High-dose | | −11.1 (7.21) | −9.0 (12.0) | (−23.0, 1.0) | |
| | | Placebo | | −9.2 (6.80) | −11.5 (10.0) | (−17.0, 8.0) | |
| HAM-0-17 | | Low-dose | | −8.3 (4.86) | −8.0 (6.0) | (−17.0, 3.0) | 0.452 |
| | | High-dose | | −10.3 (6.26) | −12.0 (11.0) | (−18.0, 1.0) | |
| | | Placebo | | −8.3 (4.98) | −7.5 (7.0) | (−18.0, −1.0) | |
| HAM-A | | Low-dose | | −6.5 (4.84) | −6.0 (6.0) | (−17.0, 3.0) | 0.838 |
| | | High-dose | | −6.9 (6.24) | −9.0 (12.0) | (−16.0, 1.0) | |
| | | Placebo | | −5.7 (5.05) | −5.0 (8.0) | (−16.0, 0.0) | |
| DSSS | Depression | Low-dose | | −5.3 (5.61) | −4.0 (8.0) | (−16.0, 3.0) | 0.931 |
| | | High-dose | | −5.5 (5.58) | −5.0 (5.0) | (−18.0, 3.0) | |
| | | Placebo | | −4.6 (5.53) | −2.5 (7.0) | (−14.0, 4.0) | |
| | Somatic | Low-dose | | −3.3 (3.35) | −4.0 (3.0) | (−9.0, 5.0) | 0.101 |
| | | High-dose | | −3.1 (4.60) | −3.0 (7.0) | (−11.0, 6.0) | |
| | | Placebo | | −1.3 (2.05) | −1.0 (3.0) | (−6.0, 2.0) | |
| | Pain | Low-dose | | −1.5 (2.20) | −2.0 (3.0) | (−4.0, 4.0) | 0.745 |
| | | High-dose | | −1.4 (2.85) | −1.0 (3.0) | (−9.0, 3.0) | |
| | | Placebo | | −1.1 (1.79) | −1.0 (2.0) | (−5.0, 2.0) | |
| CGI | CGI-S | Low-dose | | −1.0 (1.07) | −1.0 (1.0) | (−3.0, 1.0) | 0.679 |
| | | High-dose | | −1.2 (0.77) | −1.0 (1.0) | (−2.0, 0.0) | |
| | | Placebo | | −1.0 (0.78) | −1.0 (2.0) | (−2.0, 0.0) | |
| | CGI-I (original score) | Low-dose | | 2.9 (1.33) | (3.0, 1.0) | (1.0, 6.0) | 0.494 |
| | | High-dose | | 2.5 (0.83) | (2.0, 1.0) | (2.0, 4.0) | |
| | | Placebo | | 2.9 (0.95) | (3.0, 1.0) | (2.0, 5.0) | |

| Scale | | Treatment Group | Sample size (N) | Week 6 | | | |
|---|---|---|---|---|---|---|---|
| | | | | Mean (SD) | Median (IQR) | (Min, Max) | P-value[1] |
| MADRS | | Low-dose | 15 | −10.4 (5.18) | −9.0 (9.0) | (−17.0, −2.0) | 0.489 |
| | | High-dose | 15 | −13.4 (9.70) | −12.0 (17.0) | (−30.0, −1.0) | |
| | | Placebo | 14 | −8.6 (7.61) | −8.5 (12.0) | (−21.0, 5.0) | |
| HAM-D-17 | | Low-dose | 15 | −10.0 (5.49) | −12.0 (6.0) | (−19.0, 1.0) | 0.392 |
| | | High-dose | 15 | −11.1 (7.16) | −12.0 (13.0) | (−21.0, 3.0) | |
| | | Placebo | 14 | −7.9 (7.27) | −7.0 (9.0) | (−21.0, 7.0) | |
| HAM-A | | Low-dose | 15 | −8.3 (5.94) | −9.0 (10.0) | (−16.0, 3.0) | 0.300 |
| | | High-dose | 15 | −8.4 (5.58) | −8.0 (11.0) | (−17.0, −1.0) | |
| | | Placebo | 14 | −5.1 (6.32) | −4.5 (9.0) | (−18.0, 3.0) | |
| DSSS | Depression | Low-dose | 15 | −5.6 (5.12) | −5.0 (7.0) | (−16.0, 2.0) | 0.680 |
| | | High-dose | 15 | −6.1 (7.79) | −4.0 (11.0) | (−22.0, 8.0) | |
| | | Placebo | 14 | −3.7 (4.91) | −3.5 (4.0) | (−13.0, 7.0) | |

TABLE 6-continued

The score change of all rating scales from baseline to Week 2, 4, 6 and 7 - PP population, Part II

| | | Treatment | | | | | |
|---|---|---|---|---|---|---|---|
| | Somatic | Low-dose | 15 | −3.2 (4.06) | −3.0 (6.0) | (−10.0, 6.0) | 0.780 |
| | | High-dose | 15 | −2.8 (5.93) | −1.0 (8.0) | (−16.0, 5.0) | |
| | | Placebo | 14 | −2.7 (2.52) | −2.5 (4.0) | (−7.0, 1.0) | |
| | Pain | Low-dose | 15 | −1.5 (2.07) | −2.0 (2.0) | (−4.0, 4.0) | 0.583 |
| | | High-dose | 15 | −1.0 (3.44) | −1.0 (6.0) | (−9.0, 4.0) | |
| | | Placebo | 14 | −1.7 (1.77) | −2.0 (3.0) | (−5.0, 1.0) | |
| CGI | CGI-S | Low-dose | 15 | −1.1 (0.74) | −1.0 (1.0) | (−2.0, 0.0) | 0.442 |
| | | High-dose | 15 | −1.3 (1.23) | −1.0 (2.0) | (−3.0, 1.0) | |
| | | Placebo | 14 | −0.8 (1.05) | −1.0 (2.0) | (−2.0, 1.0) | |
| | CGI-I (original score) | Low-dose | 15 | 2.5 (0.74) | 3.0 (1.0) | (1.0, 4.0) | 0.538 |
| | | High-dose | 15 | 2.7 (1.49) | 2.0 (2.0) | (1.0, 6.0) | |
| | | Placebo | 14 | 3.1 (1.21) | 3.0 (1.0) | (2.0, 6.0) | |

| | | Treatment | Week 7 | | | |
|---|---|---|---|---|---|---|
| | Scale | Group | Mean (SD) | Median (IQR) | (Min, Max) | P-value[1] |
| | MADRS | Low-dose | −9.1 (4.80) | −8.0 (9.0) | (−17.0, −3.0) | 0.295 |
| | | High-dose | −13.9 (8.97) | −12.0 (13.0) | (−32.0, −3.0) | |
| | | Placebo | −10.0 (6.91) | −9.50 (7.0) | (−23.0, 5.0) | |
| | HAM-D-17 | Low-dose | −8.8 (5.45) | −9.0 (11.0) | (−18.0, 1.0) | 0.431 |
| | | High-dose | −10.8 (6.53) | −11.0 (6.0) | (−22.0, 5.0) | |
| | | Placebo | −8.6 (6.54) | −7.5 (12.0) | (−22.0, −1.0) | |
| | HAM-A | Low-dose | −5.9 (5.93) | −4.0 (11.0) | (−15.0, 3.0) | 0.330 |
| | | High-dose | −9.0 (6.22) | −8.0 (9.0) | (−22.0, 0.0) | |
| | | Placebo | −5.8 (6.19) | −5.0 (13.0) | (−15.0, 3.0) | |
| DSSS | Depression | Low-dose | −5.0 (5.44) | −5.0 (7.0) | (−16.0, 6.0) | 0.387 |
| | | High-dose | −6.7 (5.61) | −7.0 (8.0) | (−18.0, 1.0) | |
| | | Placebo | −3.4 (5.94) | −3.0 (8.0) | (−13.0, 7.0) | |
| | Somatic | Low-dose | −3.1 (2.75) | −3.0 (4.0) | (−9.0, 1.0) | 0.372 |
| | | High-dose | −3.3 4.08) | −2.0 (7.0) | (−11.0, 3.0) | |
| | | Placebo | −1.6 (3.01) | −1.0 (3.0) | (−8.0, 5.0) | |
| | Pain | Low-dose | −1.4 (1.72) | −1.0 (3.0) | (−5.0, 1.0) | 0.579 |
| | | High-dose | −1.3 (2.47) | −1.0 (5.0) | (−6.0, 3.0) | |
| | | Placebo | −0.8 (2.15) | 0.0 (4.0) | (−4.0, 2.0) | |
| CGI | CGI-S | Low-dose | −1.3 (0.70) | −1.0 (1.0) | (−2.0, 0.0) | 0.406 |
| | | High-dose | −1.5 (1.13) | −1.0 (1.0) | (−4.0, 0.0) | |
| | | Placebo | −0.9 (0.92) | −1.0 (2.0) | (−2.0, 1.0) | |
| | CGI-I (original score) | Low-dose | 2.7 (0.72) | 3.0 (1.0) | (1.0, 4.0) | 0.156 |
| | | High-dose | 2.4 (0.83) | 2.0 (1.0) | (1.0, 4.0) | |
| | | Placebo | 3.1 (1.10) | 3.0 (2.0) | (2.0, 6.0) | |

[1]Kruskal-Wallis test.

MADRS = Montgomery-Åsberg Depression Rating Scale; HAM-D-17 = Hamilton Rating Scale for Depression; HAM-A = Hamilton Rating Scale for anxiety; DSSS = Depression and Somatic Symptoms Scale; CGI = Clinical Global Impression; CGI-S = CGI-severity; CGI-I = CGI-improvement.

What is claimed is:

1. A method of treating major depressive disorder (MDD) comprising orally administering to a subject in need thereof a composition containing an amount of a botanical extraction at a daily dose of 2280-3800 mg; wherein the botanical extraction is one or a combination of:
   (i) a polar solvent extract from dry root of *Polygala tenuifolia* Willd, the polar solvent being water, a mixture of water and methanol, or a mixture of water and ethanol;
   (ii) an aqueous fraction resulting from an extraction of the polar solvent extract of (i) with an organic solvent;
   (iii) an organic eluent by introducing the polar solvent extract of (i) or the aqueous fraction of (ii) into a reverse phase chromatography column, and eluting the column with water and an organic solvent; and
   (iv) a filtrate having a molecular mass less than 30,000 in the organic eluent of (iii).

2. The method of claim 1, wherein the composition is administered in an oral dosage form.

3. The method of claim 1, wherein the composition further contains silicon dioxide and magnesium stearate and is in a form of a capsule.

4. The method of claim 3, wherein the composition is administered at an onset of an episode of a symptom of the depressive disorder.

5. The method of claim 3, wherein the composition is administered chronically.

6. The method of claim 5, wherein the composition is administered on a schedule throughout the day.

7. The method of claim 6, wherein the said daily dose is administered once per day, twice per day, or three times per day.

8. The method of claim 7, wherein each dose is 760 mg of the botanical extraction.

9. The method of claim 8, wherein the administration is daily over at least 25 days.

10. The method of claim 5, wherein the said subject is under evaluation at an end of administration and after at least one month thereafter.

11. The method of claim 10, wherein the said evaluation comprises administering and evaluating results of the Montgomery-Asberg Depression Rating Scale (MADRS), the Hamilton Depression Rating Scale (HAM-D-17), the Hamilton Anxiety Rating Scale (HAM-A), the Clinical Global Impression Scale (CGI), the Columbia-Suicide Severity Rating Scale (C-SSRS), or a combination thereof.

* * * * *